(12) United States Patent  
Grassl

(10) Patent No.: US 8,165,655 B2  
(45) Date of Patent: Apr. 24, 2012

(54) MEDICAL ELECTRODE

(75) Inventor: Thomas Grassl, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 894 days.

(21) Appl. No.: 12/206,980

(22) Filed: Sep. 9, 2008

(65) Prior Publication Data

US 2009/0076365 A1  Mar. 19, 2009

(30) Foreign Application Priority Data

Sep. 14, 2007 (DE) .......................... 10 2007 044 019

(51) Int. Cl.
*A61B 5/04* (2006.01)
*A61N 1/04* (2006.01)
(52) U.S. Cl. ........ 600/392; 600/391; 607/149; 607/152; 607/153
(58) Field of Classification Search .................. 600/391, 600/392; 607/149.152, 153
See application file for complete search history.

(56) References Cited

U.S. PATENT DOCUMENTS

| 4,798,208 A | 1/1989 | Faasse, Jr. |
| 4,899,754 A * | 2/1990 | Bly et al. ....................... 600/392 |
| 6,240,323 B1 | 5/2001 | Calenzo, Sr. et al. |
| 2009/0076583 A1 * | 3/2009 | Schermeier et al. .......... 607/149 |

FOREIGN PATENT DOCUMENTS

| DE | 71 32 867 U | 2/1973 |
| DE | 86 24 683 U1 | 10/1986 |
| EP | 0 862 924 A | 9/1998 |
| WO | WO 00/09202 A | 2/2000 |

* cited by examiner

*Primary Examiner* — Lee Cohen  
(74) *Attorney, Agent, or Firm* — McGlew and Tuttle, P.C.

(57) ABSTRACT

A medical electrode is provided for detecting and transmitting electric pulses from the body surface of a patient to an electric pulse processor. The medical electrode includes an outer carrier and at least one inner carrier (3, 3', 3''). The outer carrier and the inner carrier are connected at a defined number of geometrically distributed points (2). The points (2) form an outer edge (4) of the inner carrier and are perforated, so that the outer carrier and the inner carrier can be separated at these points (2). An adhesion area (5) is formed on the underside of the outer carrier (1) and of the inner carrier for adhering the medical electrode to the patient body surface. A contact element (7) is provided with a conductive area arranged concentrically to the contact element (7) for establishing contact with the body surface of the patient. The contact element (7) and the conductive area (8) are arranged within the inner carrier.

20 Claims, 4 Drawing Sheets

MEDICAL ELECTRODE

CROSS REFERENCE TO RELATED APPLICATIONS

This application claims the benefit of priority under 35 U.S.C. §119 of German Patent Application DE 10 2007 044 019.9 filed Sep. 14, 2007, the entire contents of which are incorporated herein by reference.

FIELD OF THE INVENTION

The present invention pertains to a medical electrode.

BACKGROUND OF THE INVENTION

Medical electrodes for detecting and transmitting electric pulses from the body surface of an patient to a electric pulse processor are known from medical practice. Medical electrodes of various dimensions are available for different applications and corresponding to the patient's size. For example, electrodes with a diameter of approximately 15 mm are used in the field of neonatal medicine, whereas electrodes for adults may have a diameter ranging from about 25 mm to 60 mm. Thus, the large number of medical electrodes of different sizes has proved to be disadvantageous in medical practice. For example, medical electrodes of at least three different sizes must be kept ready, namely, for neonates and for adults of a small, medium or large size. This requires an increased logistical effort for both the manufacturer and/or distributor of the medical electrodes and the user in medical practice.

SUMMARY OF THE INVENTION

An object of the present invention is to propose a medical electrode by means of which the indicated drawbacks of the state of the art can be overcome.

A medical electrode for detecting and transmitting electric pulses from the body surface of a patient to a means for processing electric pulses, which medical electrode has at least one outer carrier and at least one inner carrier, is proposed according to the present invention, where the outer carrier and the at least one inner carrier are connected at a defined number of geometrically distributed points, and these points form an outer edge of the at least one inner carrier and are perforated, so that the outer carrier and the at least one inner carrier can be separated at the points. Furthermore, an adhesion area, for adhering the medical electrode to the body surface of the patient, is formed on the underside of each of the outer carrier and of the at least one inner carrier. A conductive area for establishing contact with the body surface of the patient is arranged concentrically to a contact element, and the contact element and the conductive area are arranged within the at least one inner carrier.

The structure of the medical electrode according to the present invention makes it possible in a simple manner to change the medical electrode from a larger shape to a smaller shape before use on a patient. The dimensions of the outer carrier correspond here to the electrode of the larger shape and the dimensions of the at least one inner carrier to the electrode of the smaller shape. An outer edge of the medical electrode according to the present invention can preferably have a nearly oval shape. In another advantageous embodiment of the medical electrode according to the present invention, the outer edge of the outer carrier may have a rectangular, preferably square shape.

At least two medical electrodes of different sizes can be advantageously made available to the user with the medical electrode according to the present invention, and the user can prepare the particular electrode size necessary in a simple manner and rapidly.

One advantage is, moreover, that only one product must be kept in stock in clinical practice with the medical electrode according to the present invention for application on at least two patients of different sizes.

The inner carrier of the medical electrode according to the present invention is designed in another preferred embodiment as a first inner carrier and as a second inner carrier. The first and second inner carriers are connected in this embodiment at a defined number of geometrically distributed points, and the points form an outer edge of the first inner carrier and are perforated, so that the first inner carrier and the second inner carrier can be separated at these points. Three different electrode sizes can be made available with this embodiment.

In yet another preferred embodiment, the medical electrode according to the present invention has a gripping area, which is defined by a part of the outer edge of the at least one inner carrier, and this part of the outer edge is preferably continuously perforated. The inner carrier can thus be separated from the outer carrier of the medical electrode according to the present invention in a simple manner if a smaller electrode size is needed.

In one embodiment of the medical electrode according to the present invention with three different electrode sizes, i.e., with a first electrode size corresponding to the dimensions of the outer carrier, with a second electrode size corresponding to the dimensions of the second inner carrier and with a third electrode size corresponding to the dimensions of the first inner carrier, the gripping area of the first inner carrier and the gripping area of the second inner carrier are advantageously arranged opposite each other. This embodiment makes optimal handling possible in connection with the selection and preparation of the corresponding electrode size before the use of that electrode.

The present invention will be explained in more detail with reference to the attached drawings, where identical reference numbers designate identical structures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
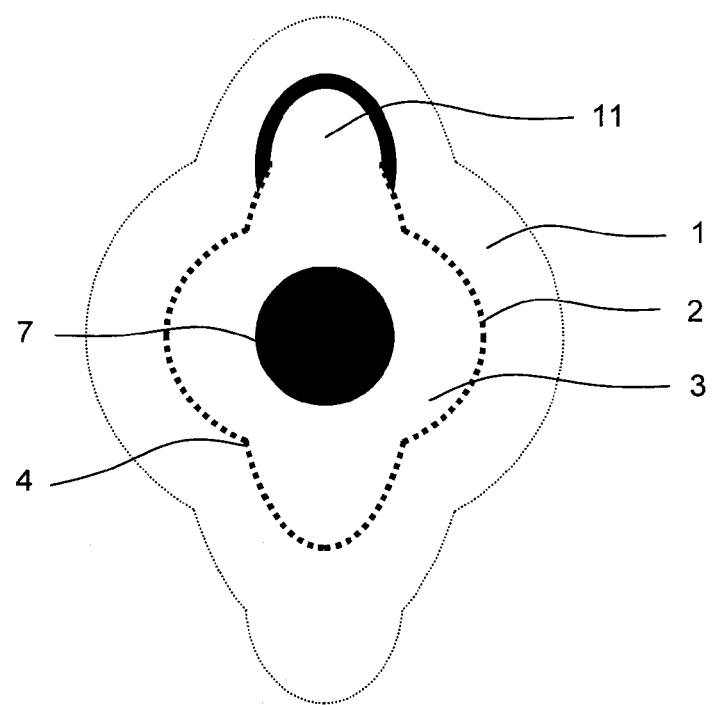
FIG. 1 is a top view of a medical electrode according to the present invention.

Referring to the drawings in particular, as can be recognized from the view in FIG. 1, the medical electrode according to the present invention has an outer carrier 1 and an inner carrier 3.

The outer carrier 1 and the inner carrier 3 are connected at a defined number of geometrically distributed points 2. The points form an outer edge 4 of the inner carrier 3 and are perforated. The points 2 are perforated such that the inner carrier 3 and the outer carrier 1 can be separated. The medical electrode according to the present invention can thus be prepared in a corresponding size according to the size of the patient in a simple manner and rapidly. The inner carrier 3 is separated for this from the outer carrier 1. The inner carrier 3 is advantageously made now with a gripping area 11, which is defined by a part of the outer edge 4 of the inner carrier 3. The edge area of the gripping area 11, which coincides with a part of the outer edge 4 of the inner carrier 3, is preferably perforated continuously. This makes possible the simple separation of the inner carrier 3 from the outer carrier 1. The inner carrier 3 forms, together with the outer carrier 1, the base of the medical electrode according to the present invention in the largest dimension for use for large patients. The medical electrode according to the present invention with the base of the inner carrier 3 is used for smaller patients, e.g., children. The diameter of the outer carrier 1 may be in the range of 55 mm to 60 mm, which corresponds to a maximum electrode size for adults. The diameter of the outer carrier 1 is preferably 60 mm. The inner carrier 3 preferably has a diameter of 30 mm.

The carrier material advantageously consists of a foamed or textile material, for example, a plaster material.

The outer carrier 1 is advantageously designed to have a nearly oval shape. Collisions of the medical electrode according to the present invention, for example, in case of a thoracic wall lead, can thus be avoided.

The medical electrode according to the present invention is provided with a contact element 7 in its center, around which a conductive area 8 (FIG. 2) extends coaxially. The contact element 7 is provided with a cable for connection to a electric pulse processor (not shown). The contact element 7 and the conductive area 8 are arranged within the inner carrier 3. The contact element 7 may have a material consisting of steel and silver chloride. In an especially preferred embodiment, the contact element 7 is made of carbon. The cable for connection to the means for processing electric pulses may be connected to the contact element 7 via a welded connection.

Figure 2:
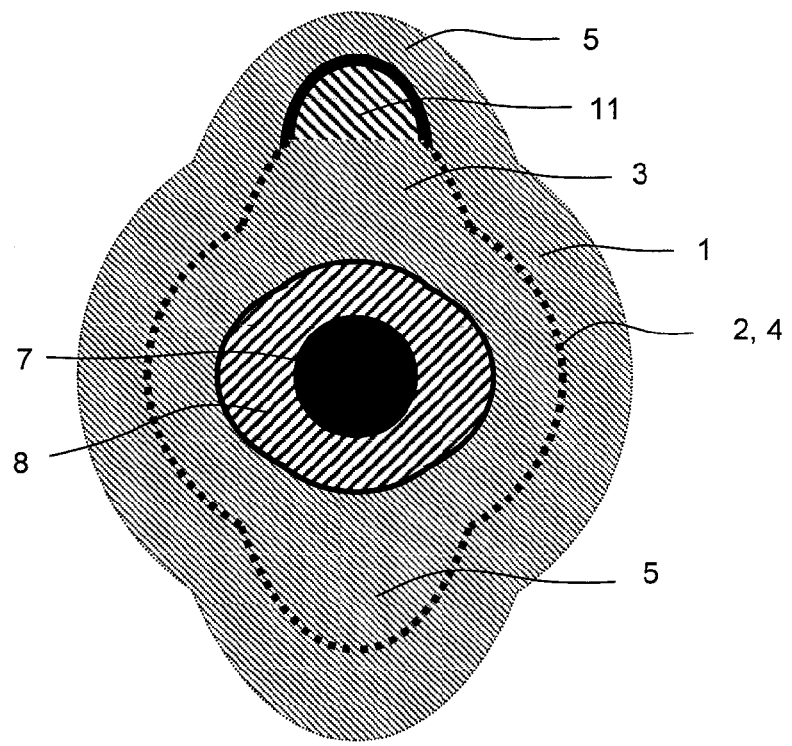
FIG. 2 is a bottom view of the medical electrode according to the present invention from FIG. 1.

The electric pulses are detected by the conductive area 8 shown in the view in FIG. 2 from the body surface of the patient and sent via the contact element 7 and the cable to the means for processing the electrical pulses. The conductive area 8 is provided with a layer of hydrogel. The dimensions of both the conductive area 8 and of the contact element 7 are the same for all final dimensions of the medical electrode according to the present invention. Good signal quality of the electric pulses is thus guaranteed.

The medical electrode according to the present invention has, furthermore, an adhesion area 5 each on the underside of the outer carrier 1 and of the inner carrier 3 (FIG. 2), the adhesion areas making it possible to attach the electrode to the body surface of the patient. With the exception of a gripping area 11 and the conductive area 8, the adhesion area 5 preferably extends over the complete lower surface of the medical electrode according to the present invention. The adhesion area 5 is covered with a protective cover 9 (FIG. 3), which is to be peeled off before use, the protective cover 9 preferably being made without perforations. When using the medical electrode according to the present invention and when selecting an electrode size, which corresponds to the base of the inner carrier 3, the protective cover 9 can be advantageously removed from the underside of the medical electrode in a first step before the inner carrier 3 with the gripping area 11 is detached from the outer carrier 1 and is attached in a corresponding position on the body surface of the patient in another step.

Figure 3:
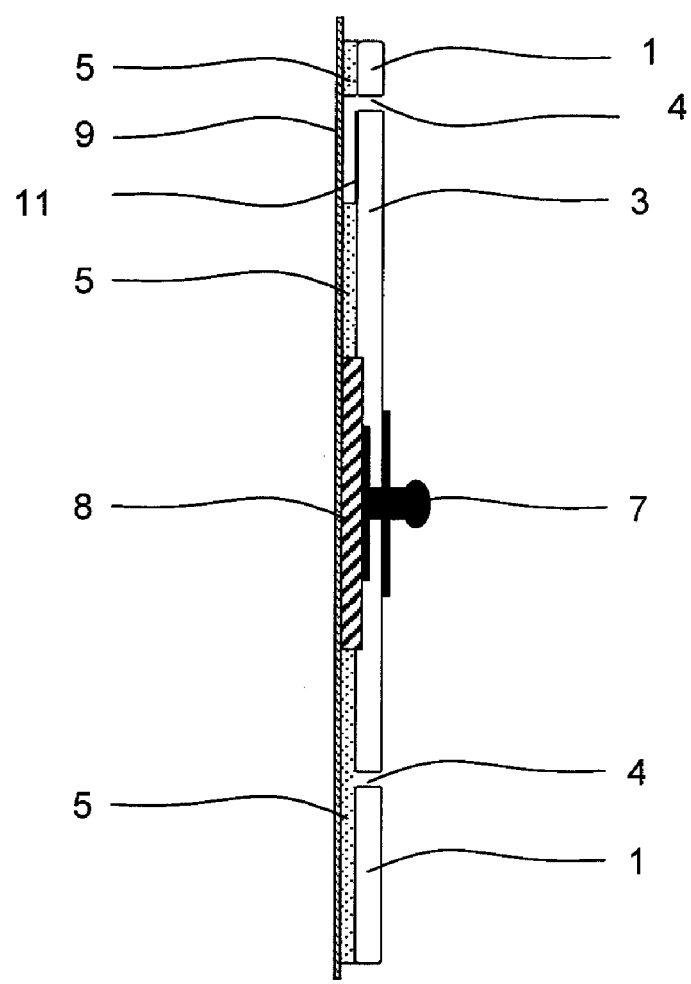
FIG. 3 is a sectional view through the vertical axis of the medical electrode according to the present invention from FIG. 1.

To illustrate the structure of the medical electrode according to the present invention shown in FIG. 1, FIG. 3 shows a sectional view through the vertical axis.

Figure 4A:
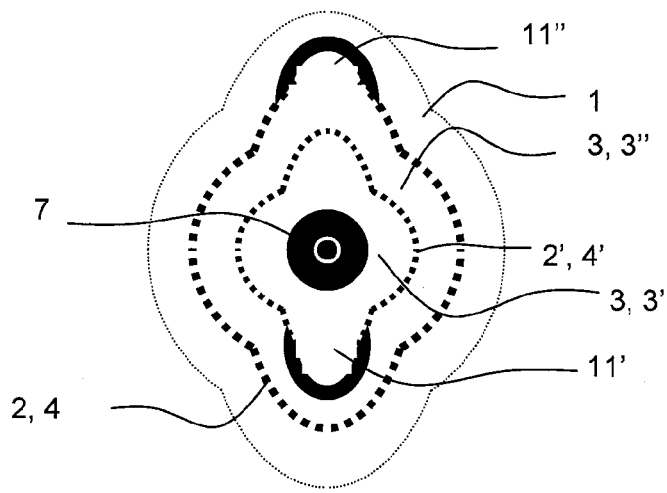
FIG. 4A is a view of a medical electrode according to the present invention with three different electrode sizes with two inner carriers and an outer carrier.

The view in FIG. 4A shows a medical electrode according to the present invention with three different electrode sizes, with two inner carriers and one outer carrier.

It can be clearly recognized that the inner carrier 3 is designed as a first inner carrier 3' and as a second inner carrier 3", the first and second inner carriers 3', 3" being connected at a defined number of geometrically distributed points 2', said points 2' forming an outer edge 4' of the first inner carrier 3' and being perforated. The first inner carrier 3' is arranged such that it is surrounded by the second inner carrier 3", which is in turn surrounded by the outer carrier 1. Points 2' are perforated such that the first inner carrier 3' and the second inner carrier 3" can be separated at these points 2'.

Figures 4B, 4C, 4D:
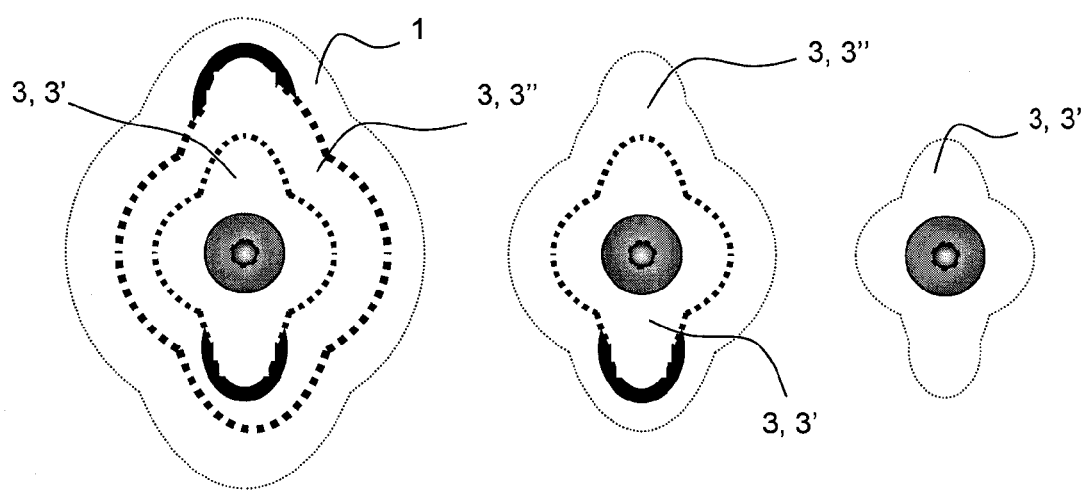
FIG. 4B is a view of the medical electrode according to the present invention of a size corresponding to the dimensions of the outer carrier.
FIG. 4C is a view of the medical electrode according to the present invention of a size corresponding to the dimensions of the second inner carrier.
FIG. 4D is a view of the medical electrode according to the present invention of a size corresponding to the dimensions of the first inner carrier.

Both the first inner carrier 3' and the second inner carrier 3" have a gripping area 11' and 11" each, which are advantageously arranged opposite each other. Easy separation of both the first inner carrier 3' from the second inner carrier 3" and of the first inner carrier 3' and of the second inner carrier 3" from the outer carrier 1 is made possible in this embodiment of the medical electrode according to the present invention. The second inner carrier 3" may be used with a diameter in the range of approximately 15 mm to 20 mm in neonatal medicine. The views according to FIGS. 4B through 4D show the three electrodes of different sizes, which can be made available from the medical electrode according to the present invention according to the view in FIG. 4A. FIG. 4B shows the medical electrode according to the present invention in the size corresponding to the dimensions of the outer carrier 1. The first inner carrier 3', the second inner carrier 3" and the outer carrier 1 are connected in this embodiment. FIG. 4C shows the medical electrode according to the present invention in the size corresponding to the dimensions of the second inner carrier 3", in which the outer carrier 1 is separated from the second inner carrier 3". FIG. 4D shows the medical electrode according to the present invention in the size corresponding to the dimensions of the first inner carrier 3', in which the first inner carrier 3' is separated from the second inner carrier 3" and from the outer carrier 1.

Figure 5:
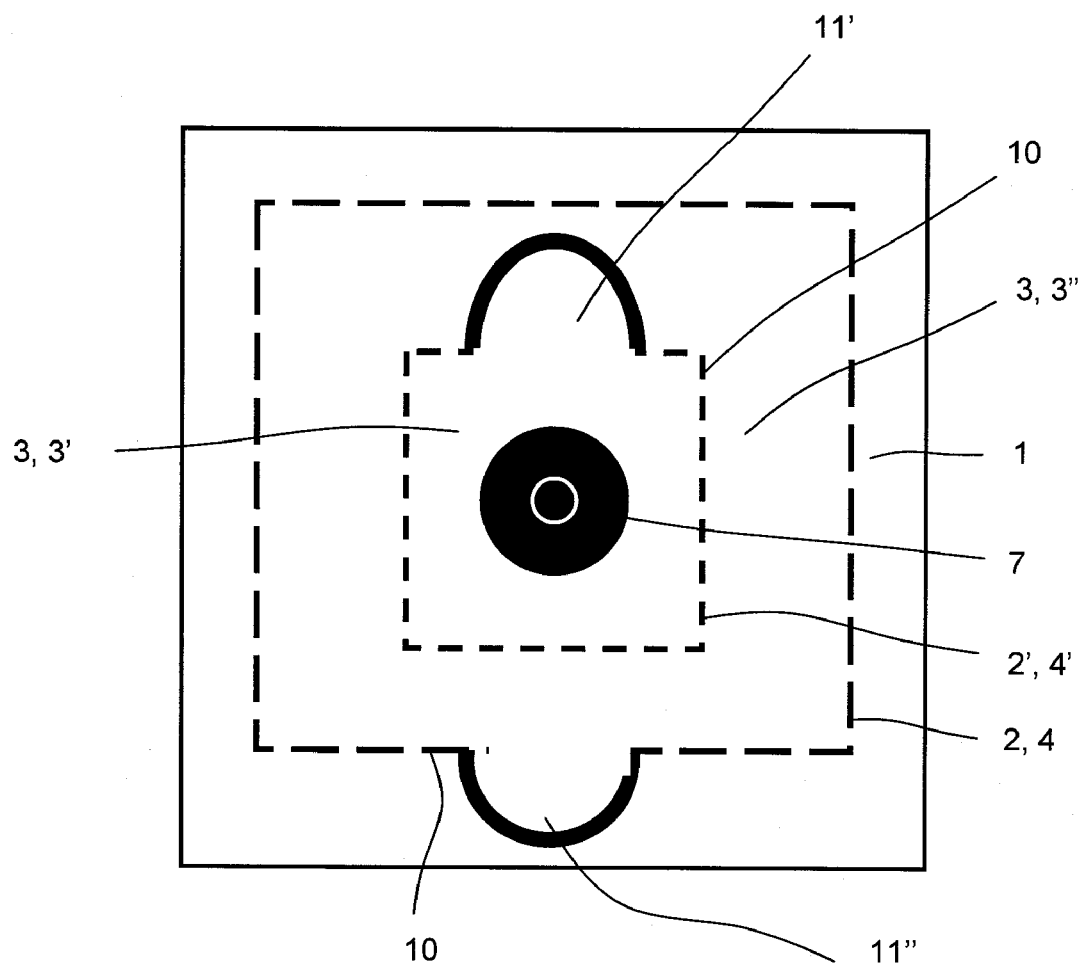
FIG. 5 is a view of an embodiment of the medical electrode according to the present invention with a square shape.

FIG. 5 shows another possible design of the medical electrode according to the present invention. The outer carrier 1, the first inner carrier 3' and the second inner carrier 3" have a square shape. The medical electrode according to the present invention shown in the view in FIG. 5 makes possible three different sizes in this embodiment. Points 2 form a square outer edge 4 of the second inner carrier 3". Points 2 form a square outer edge 4' of the first inner carrier 3'.

Corresponding to the view in FIG. 5, the perforated points 2 and 2' may be advantageously designed in the form of elongated holes 10. The particular gripping area 11' and 11" of the first inner carrier 3' and of the second inner carrier 3" are, in turn, advantageously arranged opposite each other. Cutting wastes during preparation can be minimized with this square design of the medical electrode according to the present invention, and the manufacturing costs can be advantageously reduced.

The solution according to the present invention provides a medical electrode for both neonates and adult patients of various sizes, which can be prepared by the user in the particular size in a simple manner and rapidly. This makes possible cost-effective logistics and the use of the medical electrode according to the present invention for various applications.

While specific embodiments of the invention have been shown and described in detail to illustrate the application of the principles of the invention, it will be understood that the invention may be embodied otherwise without departing from such principles.

LIST OF REFERENCE NUMBERS

1 Outer carrier
2, 2' Geometrically distributed points
3 Inner carrier
3' First inner carrier
3" Second inner carrier
4 Outer edge of inner carrier/second inner carrier
4' Outer edge of first inner carrier
5 Adhesion area
7 Contact element
8 Conductive area
9 Protective cover
10 Elongated holes
11 Gripping area of inner carrier
11' Gripping area of first inner carrier
11" Gripping area of second inner carrier

What is claimed is:

1. A medical electrode for detecting and transmitting electric pulses from a body surface of a patient to an electric pulse processor, the medical electrode comprising:
an outer carrier;
an inner carrier, wherein said outer carrier and said inner carrier are connected at a defined number of geometrically distributed points, wherein said geometrically distributed points form an outer edge of said inner carrier and are perforated, whereby said outer carrier and said inner carrier can be separated at said outer edge, said inner carrier having a gripping area which is defined by a part of said outer edge of said inner carrier, wherein said part of the outer edge is perforated continuously to fully separate said inner carrier from said outer carrier along said part of the outer edge of said inner carrier;
an adhesion area formed on an underside of said outer carrier and said inner carrier for adhering the medical electrode to the body surface of the patient, said adhesion area extending along said underside of said inner carrier to a region adjacent to said gripping area with said adhesion area interrupted in said gripping area such that said gripping area is free of adhesive;
a contact element; and
a conductive area arranged concentrically to said contact element for establishing contact with the body surface of the patient, wherein said contact element and said conductive area are arranged within said inner carrier.

2. A medical electrode in accordance with claim 1, further comprising a protective cover, which is to be peeled off before use, formed on an underside of said adhesion area, said adhesion area including adhesive at a portion of said underside of said outer carrier directly adjacent to said part of the outer edge of said inner carrier, bordering along a full length of said part of the outer edge of said inner carrier.

3. A medical electrode in accordance with claim 2, wherein said outer carrier has a nearly oval shape.

4. A medical electrode in accordance with claim 2, wherein said outer carrier has a rectangular shape.

5. A medical electrode in accordance with claim 2, wherein said inner carrier comprises a first inner carrier and a second inner carrier, wherein said first inner carrier and said second inner carrier are connected at a defined number of geometrically distributed inner carrier points, wherein said inner carrier points form an outer edge of the first inner carrier and are perforated, so that said first inner carrier and said second inner carrier can be separated at said inner carrier points.

6. A medical electrode in accordance with claim 5, wherein: said gripping area is a second inner carrier gripping area and said first inner carrier has a first inner carrier gripping area arranged opposite said second inner carrier gripping area, said first inner carrier gripping area being defined by a part of said outer edge of said first inner carrier perforated continuously to separate said first inner carrier from said second inner carrier along said part of said outer edge of said first inner carrier, wherein said underside of said inner carrier is free of adhesive in said first inner carrier gripping area.

7. A medical electrode in accordance with claim 2, wherein said outer carrier and said inner carrier consist of a foamed or textile material.

8. A medical electrode in accordance with claim 2, wherein said conductive area comprises a layer of hydrogel.

9. A medical electrode in accordance with claim 2, wherein said contact element is provided with a cable for connection to the electric pulse processor, and said cable and said contact element are connected by a welded connection.

10. A medical electrode in accordance with claim 2, wherein said contact element is made of carbon.

11. A medical electrode in accordance with claim 2, wherein said perforated points are in the form of elongated holes.

12. A medical electrode for detecting and transmitting electric pulses from a body surface of a patient to an electric pulse processor, the medical electrode comprising:
an outer carrier;
an inner carrier, wherein said outer carrier and said inner carrier are connected at an outer edge of said inner carrier with said edge comprising perforations, whereby said outer carrier and said inner carrier can be separated at said perforations;
an outer carrier adhesion area formed on an underside of said outer carrier;
an inner carrier adhesion area formed on an underside of said inner carrier, said outer carrier adhesion area and said inner carrier adhesion area for adhering the medical electrode to the body surface of the patient, said inner carrier having an outer edge portion that is fully separated from said outer carrier over a gripping edge length, said outer edge portion gripping edge length defining a user gripper means for gripping said inner carrier, said outer edge portion being located adjacent to said inner carrier adhesion area, wherein adhesive is not applied to said user gripper means defined by said outer edge portion and said adhesion area is interrupted to form a gripping area of said gripper means such that said gripping area is free of adhesive;

a contact element; and a conductive area arranged at a side of said contact element for establishing contact with the body surface of the patient, wherein said contact element and said conductive area are arranged connected to said inner carrier.

13. A medical electrode in accordance with claim 12, wherein said adhesion area includes adhesive at a portion of said underside of said outer carrier directly adjacent to said outer edge portion and fully bordering said outer edge portion over said gripping edge length.

14. A medical electrode in accordance with claim 13, wherein said inner carrier comprises a first inner carrier and a second inner carrier, wherein said first inner carrier and said second inner carrier are connected at an outer edge of the first inner carrier with said outer edge of the first inner carrier comprising inner carrier perforations whereby said first inner carrier and said second inner carrier can be separated at said inner carrier perforations.

15. A medical electrode in accordance with claim 13, further comprising a protective cover, which is to be peeled off before use, formed on an underside of said outer carrier and said inner carrier and in contact with said adhesion area.

16. A medical electrode in accordance with claim 13, wherein said outer carrier and said inner carrier comprise one of a foamed material and a textile material and said conductive area comprises a layer of hydrogel.

17. A medical electrode in accordance with claim 13, wherein said contact element is made of carbon.

18. A medical electrode for detecting and transmitting electric pulses from a body surface of a patient to an electric pulse processor, the medical electrode comprising:

an outer carrier;

an inner carrier, wherein said outer carrier and said inner carrier are connected at a defined number of geometrically distributed points, wherein said geometrically distributed points form an outer edge of said inner carrier and are perforated, whereby said outer carrier and said inner carrier can be separated at said outer edge, said inner carrier having a gripping area which is defined by a part of an outer edge of said inner carrier, wherein said part of the outer edge is perforated continuously to separate the inner carrier from the outer carrier along said part of the outer edge of said inner carrier;

an adhesion area formed on an underside of said outer carrier and said inner carrier for adhering the medical electrode to the body surface of the patient, said adhesion area extending along said underside of said inner carrier to a region adjacent to said gripping area with said gripping area being free of adhesive and with adhesive at a portion of said underside of said outer carrier directly adjacent to said part of the outer edge of said inner carrier and bordering along a full length of said part of the outer edge of said inner carrier;

a contact element; and a conductive area arranged concentrically to said contact element for establishing contact with the body surface of the patient, wherein said contact element and said conductive area are arranged within said inner carrier.

19. A medical electrode in accordance with claim 18, wherein said inner carrier comprises a first inner carrier and a second inner carrier, wherein said first inner carrier and said second inner carrier are connected at an outer edge of said first inner carrier with said outer edge of said first inner carrier comprising inner carrier perforations whereby said first inner carrier and said second inner carrier can be separated at said inner carrier perforations.

20. A medical electrode in accordance with claim 19, wherein said first inner carrier has a first inner carrier gripping area arranged opposite said gripping area of said inner carrier, said first inner carrier gripping area being defined by a part of said outer edge of said first inner carrier perforated continuously to separate said first inner carrier from said second inner carrier along said part of said outer edge of said first inner carrier, wherein said underside of said inner carrier is free of adhesive in said first inner carrier gripping area.

* * * * *